United States Patent [19]

Chun et al.

[11] Patent Number: 5,210,267

[45] Date of Patent: May 11, 1993

[54] OPTICALLY-ACTIVE ALIPHATIC β-HALOGEN SUBSTITUTED CARBOXYLIC ACID 4'-(4-ALKOXYBENZYLOXY)BIPHENYL THIOESTER COMPOUNDS AND PROCESS FOR THE PREPARATION THEREOF

[75] Inventors: Youngjae Chun, Euiwang; Junha Suh, Bucheon, both of Rep. of Korea

[73] Assignee: Samsung Electron Devices Co., Ltd., Rep. of Korea

[21] Appl. No.: 686,743

[22] Filed: Apr. 16, 1991

[30] Foreign Application Priority Data

Oct. 31, 1990 [KR] Rep. of Korea ............... 90-17641

[51] Int. Cl.$^5$ ............................................ C07C 327/16
[52] U.S. Cl. ................................. 558/255; 558/252; 252/299.66; 252/299.67
[58] Field of Search ............................. 558/255, 252; 252/299.1, 299.6, 299.66, 299.67

[56] References Cited

U.S. PATENT DOCUMENTS

| | | | |
|---|---|---|---|
| 4,162,988 | 7/1979 | Maze et al. | 252/299.6 |
| 4,668,427 | 5/1987 | Saito et al. | 252/299.6 |
| 4,728,458 | 3/1988 | Higuchi et al. | 252/299.6 |
| 4,751,019 | 6/1988 | Saito et al. | 252/299.6 |
| 4,753,752 | 6/1988 | Raynes et al. | 252/299.6 |
| 4,952,335 | 8/1990 | Furukawa et al. | 252/299.6 |
| 5,068,054 | 11/1991 | Betterton et al. | 558/252 |

OTHER PUBLICATIONS

Geerlhaar, "Ferroelectric Mixtures and their Physico-Chemical Properties", Ferroelectrics, 85, pp. 329-349 (1988).
An article entitled Ferroelectric S$_c^*$ Phase in some Benzoate Series by Tien et al., 1987, pp. 147-155.
An article entitled New Ferroelectric Liquid Crystals with Spontaneous Polarization Exceeding $10^{-7}$c/CM$^2$ and their Electrical and Optical Properties by Yoshino et al., 1987, pp. 87-103.
An article entitled Submicrosecond Bistable Electro-Optic Switching in Liquid Crystals by Clark et al., 1980, 899-901.
An article entitled Synthesis of Stable and Low Melting Ferroelectric Liquid Crystals of the Ester Family by Patrick Keller, 1984, pp. 3-7.
An article entitled Novel Dielectric Behavior of Ferroelectric Liquid Crystals and High-Field Effects by Yoshino et al., 1988, pp. 639-644.

Primary Examiner—Jose G. Dees
Assistant Examiner—B. Frazier
Attorney, Agent, or Firm—Christie, Parker & Hale

[57] ABSTRACT

The present invention provides novel optically-active aliphatic β-halogen substituted carboxylic acid 4'-(4-alkoxybenzyloxy)biphenyl thioester compounds of the general formula:

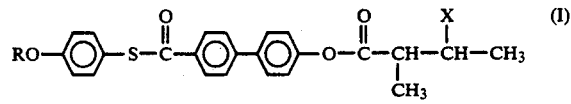

wherein R represents a straight-chained alkyl radical having C$_2$ to C$_{10}$ carbon atoms and X represents a halogen atom, and a process for the preparation thereof. The novel biphenyl thioester compounds provided according to the present invention are usable as a dopant or a base material for liquid crystal blending, thereby improving the properties of LCD.

2 Claims, No Drawings

OPTICALLY-ACTIVE ALIPHATIC β-HALOGEN SUBSTITUTED CARBOXYLIC ACID 4'-(4-ALKOXYBENZYLOXY)BIPHENYL THIOESTER COMPOUNDS AND PROCESS FOR THE PREPARATION THEREOF

BACKGROUND OF THE INVENTION

1. Field of the Invention

The present invention relates to novel optically-active aliphatic β-halogen substituted carboxylic acid 4'-(4-alkoxybenzyloxy)biphenyl thioester compounds defined by the general formula:

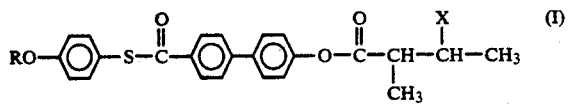

wherein R represents a straight-chained alkyl radical having $C_2$ to $C_{10}$ carbon atoms and X represents a halogen atom, and a process for the preparation thereof.

In particular, the present invention relates to novel compounds usable as a base material or a dopant for liquid crystal blending to improve the properties of LCD, and a process for the preparation thereof.

2. Description of the Prior Art

Generally, a liquid crystal phase having an optically-active group has been well-known but the fact that a portion of a smectic phase shows ferroelectricity was first discovered by R. M. Meyer.

Since this ferroelectric liquid crystal (FLC) has desired properties, such as fast response time and bistability, many specialists have taken an interest in FLC in order to apply it to color TVs, computer terminals, electrically-optical modulators, etc., utilizing such properties.

However, studies on FLC have been stagnated due to the difficulties of its applicability. After a surface stabilized ferroelectric liquid crystal (SSFLC) was made public it has become a more important material. Accordingly, various theoretical, experimental and chemical studies on FLC have been carried out in its field of application.

Since an FLC material having fast response time and bistability and being a smectic phase ($S_c^*$) in a broad temperature range is necessary in order to apply an FLC to liquid crystal display elements, several classes of an FLC substance have been synthesized to meet such conditions. In spite of all efforts, with such conventional FLC substance there is much left to be desired.

An FLC substance of cinnamate and phenyl benzoate series having the chain of

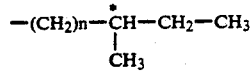

was disclosed. Recently others have studied biphenyl and benzoate series having a chiral center which can be obtained from optically-active α-amino acid. From their results, they explained that these compounds show high spontaneous polarization by introducing two adjacent asymmetric carbon atoms into the side of dipole moment and the magnitude of the spontaneous polarization depends on the size of an atom bonding to a carbon atom and the polarity.

In 1988, it was indicated by studies on p-n-alkoxy-α-methyl cinnamic acid ester derivatives, that a halogen substituent of an asymmetric carbon atom induces high spontaneous polarization by introducing a chlorine substituent into α-asymmetric carbon atom of optically-active group.

It has been found that biphenyl series are chemically stable and an ester bridge between phenyl groups has a tendency to lower the transition temperature. It has also been found that two adjacent asymmetric carbon atoms at the side of dipole moment and a halogen substituent of an asymmetric carbon atom induce high spontaneous polarization.

Thus, in a ferroelectric liquid crystal substance:
1. a rigid core
   1) is a primary basic anisotropic unit, and
   2) is a complex cyclic group as well;
2. a flexible end chain
   1) is an essential member to form liquid crystals,
   2) helps to form a declined smectic phase, and
   3) has an effect on the transition temperature by the size of its chain; and
3. the transverse dipole
   1) should be as large as possible because of its effect on formation of an FLC mesophase, and
   2) should be close to a chiral center to induce high spontaneous polarization.

On the basis of the above, a molecular design is constructed as follows:

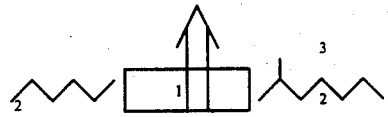

By these basic conditions, the properties of substantially practical FLC substance are as follows:
1. it should exhibit a smectic phase in the practical temperature range;
2. it should be chemically stable;
3. its spontaneous polarization should be high; and
4. its bistability should be good and response speed high.

SUMMARY OF THE INVENTION

Accordingly, an object of the present invention is to provide novel biphenyl thioester compounds and a process for the preparation thereof, which show higher spontaneous polarization by about 10 times more than the conventional ferroelectric materials, when the compounds are used as a base material or a dopant because the halogen atom with high dipole moment is adjacent to the β-asymmetric carbon atom of optically-active group and the carbonyl (C=O) bond of ester is adjacent to a core group, and which broadens a liquid crystal temperature range because a benzene ring is bonding to a thioester group by a core group.

More specifically, an object of the present invention is to provide novel biphenyl thioester compounds and a process for the preparation thereof, which are chemically stable and show a smectic phase at a practical temperature range, very high spontaneous polarization, desirable bistability and fast response time when the compounds are used as a base material or a dopant.

In order to achieve the above and other objects, the present invention provides novel optically-active aliphatic β-halogen substituted carboxylic acid 4'-(4-alkoxybenzyloxy)biphenyl thioester compounds, and a process for the preparation thereof, comprising:

reacting an optically-active β-amino acid with HF/pyridine or HCl/NaNO₂ in a solvent of distilled water under an ice bath for 7 to 10 hours to give an optically-active aliphatic β-halogen substituted carboxylic acid;

reacting said optically-active aliphatic β-halogen substituted carboxylic acid with a p-(4-hydroxyphenyl)-benzoic acid in a solvent of pyridine at a temperature of from 60° to 100° C. for 8 hours to give an optically-active aliphatic β-halogen substituted carboxylic acid p-(4-carboxy)biphenyl; and reacting said optically-active aliphatic β-halogen substituted carboxylic acid p-(4-carboxy)biphenyl with an alkoxy-thiophenol defined by the general formula:

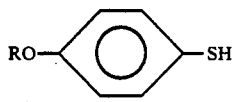

(II)

wherein R has the same meaning as defined above, by heating under reflux at a temperature of about 80° C. for about 12 hours in a solvent of pyridine.

The optically-active aliphatic β-halogen substituted carboxylic acid p-(4-carboxy)biphenyl used as the reaction material to yield the biphenyl thioester compounds according to the present invention can be prepared by reacting the optically-active β-amino acid with HF/pyridine or HCl/NaNO₂ in a solvent of distilled water under an ice bath for 7 to 10 hours to obtain aliphatic β-fluoro-or β-chlorocarboxylic acid, and then reacting said aliphatic carboxylic acid with p-(4-hydroxyphenyl)-benzoic acid defined by the general formula:

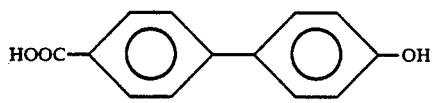

(III)

in the presence of the same solvent as described above at a temperature of from 60° to 100° C. for about 8 hours.

Alternatively, the optically-active aliphatic β-halogen substituted carboxylic acid p-(4carboxy)biphenyl compounds can be obtained at a high rate of reaction, after said aliphatic β-halogen substituted carboxylic acid is reacted with PCl₃/SOCl₂ to obtain an aliphatic β-halogen substituted acyl compound, by reacting the resulting compound with p-(4-hydroxyphenyl)-benzoic acid.

While each β-amino acids of D-type, L-type and D,L-type are available in the market, the β-amino acids of L-type are preferably selected, purified and used in the present invention.

It is also noted that the p-(4-hydroxyphenyl)benzoic acid used in the present invention can be directly synthesized in a laboratory by a conventional synthesizing method well-known to the art of organic chemistry under the reaction condition as shown below:

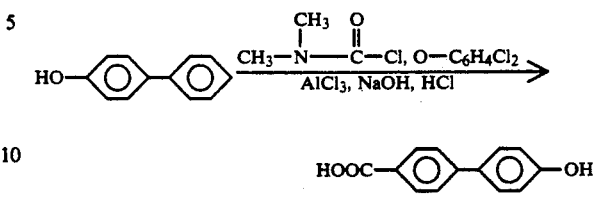

In addition, the HF/pyridine which is composed of 30% of pyridine and 70% of HF gas dissolved therein, is also available in the market and is usable in the present invention.

Since the hydrogen fluoride is in a gaseous state at ambient temperatures and therefore volatilizes readily, it should be refrigerated until ready for use. It is also advantageous to carry out the reaction under ice bath.

In addition, the novel optically-active aliphatic β-halogen substituted carboxylic acid 4'-(4-alkoxybenzyloxy)biphenyl thioester compounds according to the present invention can be obtained by reacting the optically-active aliphatic β-halogen substituted carboxylic acid p-(4-carboxy)biphenyl with the alkoxythiophenol defined by the general formula (II) below, in the presence of pyridine as a solvent by heating under reflux at a temperature of about 80° C. for 12 hours.

As described above, the alkoxythiophenol can be readily synthesized from alkoxybenzene as a starting material in a laboratory according to the conventional method well-known to the art of organic chemistry. One embodiment of the method is shown as below:

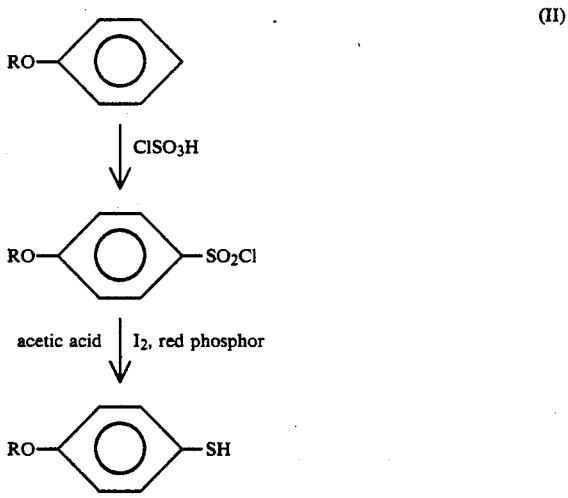

(II)

wherein R has the same meaning as previously described.

DESCRIPTION OF THE PREFERRED EMBODIMENTS

For a better understanding of the present invention, the overall reaction according to the present invention is shown by the reaction scheme below:

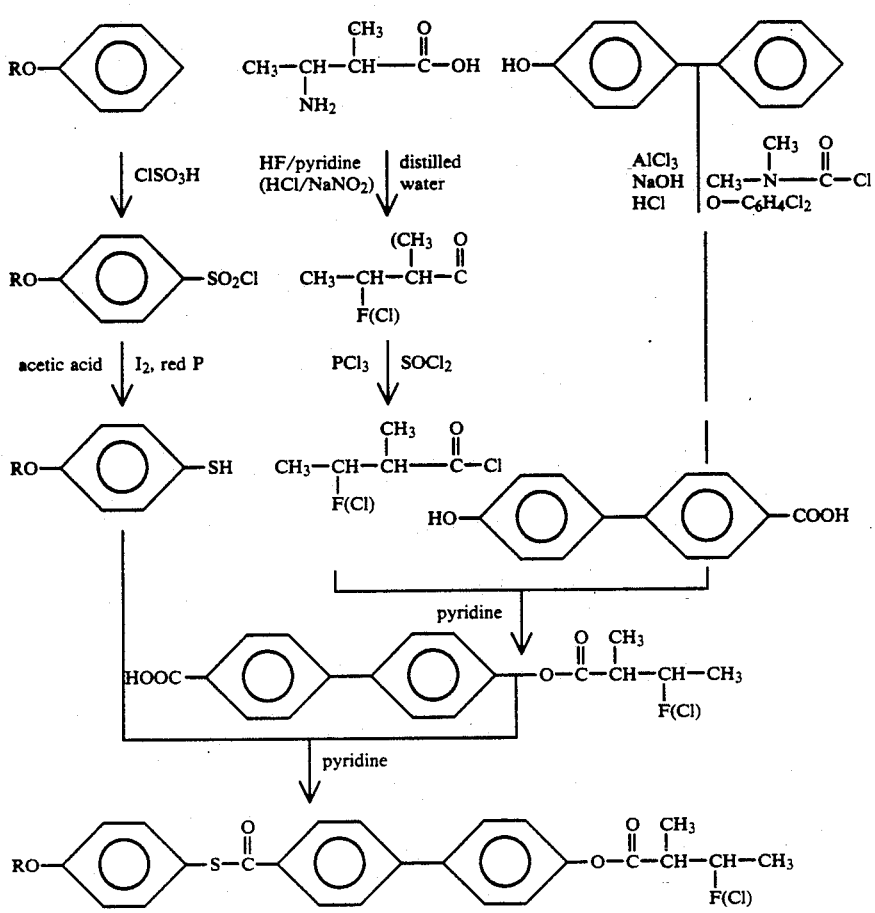

wherein R has the same meaning as previously described.

SCHEME 1

A synthesizing diagram of the biphenyl thioester compounds

Even though pyridine used as a solvent remains in the final product after completing all reaction, the new product according to the present invention can be obtained with high yield without a complicated and troublesome purification apparatus since pyridine is easily evaporated due to its low boiling point of 80° C. and removed merely by heating.

According to the present invention, the reactants in each step are preferably added in the amount of equivalent ratio.

As described above, the novel optically-active aliphatic β-halogen substituted carboxylic acid 4'-(4-alkoxybenzyloxy) biphenyl thioester compounds can be used as a dopant or a base material for liquid crystal blending, thereby broadening the extent of liquid crystal composition from the conventional ester compounds to thioester compounds, and due to the halogen atom directly bonding to the asymmetric carbon atom, the novel compounds according to the present invention improve the properties of electric field response and spontaneous polarization of liquid crystal. Further, the novel compounds according to the present invention can be used to control the liquid crystal state effectively. In this regard, the liquid crystal substance to which the novel biphenyl thioester compounds of the present invention are applied, shows improved spontaneous polarization, thereby gaining the advantages of improving the quality of LCD and the yield of the production by eliminating a twist domain when used in a display as a dopant. Thus, within the scope of the invention are dopants and base materials for liquid crystal blending which comprises, or consists essentially of, the novel optically-active aliphatic β-halogen substituted carboxylic acid 4'-(4-alkoxybenzyloxy)biphenyl thioester compounds of the invention, as well as liquid crystal substances to which said compounds are applied.

In addition, the optically-active aliphatic β-halogen substituted carboxylic acid 4'-(4-alkoxybenzyloxy)-biphenyl thioester provided according to the present invention can be used as a base material for blending.

The preferred embodiments of the present invention are hereinafter described, these examples are provided only to illustrate the present invention, and are not intended to be construed to limit or confine the scope of the present invention.

EXAMPLE 1

Preparation of (3S, 2S)-3-fluoro-2-methylbutanoic acid p-(4-carboxy)biphenyl 1.97 g. of 3-amino-2-methylbutanoic acid was dissolved in 60 ml of distilled water and then to this solution was added, dropwise, 30 ml of HF/pyridine cooled with ice. The reaction mixture was stirred under an ice bath for about thirty minutes and then 150 ml of ice water was added to the mixture. Thereafter, the mixture was dried over anhydrous magnesium sulfate and heated to remove the pyridine remaining in the product. Obtained by the foregoing was (3S, 2S)-2-methylbutanoic acid.

The above product exhibits the spectroscopic property below:

FT-IR:1200–1300 cm$^{-1}$ (C-F).

From the above spectroscopic data, it was found that the amino group in the optically-active β-amino acid was substituted with a fluorine atom.

67 g. of (3S, 2S)-3-fluoro-2-methylbutanoic acid, obtained as above, was charged into a reactor to which was also added 99 g. of p-(4-hydroxyphenyl)-benzoic acid. The reaction solution was stirred and then filtered off to obtain the title compound, i.e., the desired compound identified above.

Preparation of (3S, 2S)-3-fluoro-2-methylbutanoic acid 4'-(4-octoxybenzyloxy)biphenyl thioester 60 ml. of pyridine was charged into a reactor and then to this was added 122.1 g. of product prepared as above and 81.77 g. of octoxythiophenol. The reaction solution was heated under reflux at a temperature of 80° C. for twelve hours. After filtering off the reaction mixture, there were obtained 164 g. (83% of theoretical) of the desired title compound.

The thus obtained product was purified by column chromatography over silica gel and then identified (as follows):

NMR (CDCl$_3$, ppm): δ=0.69~1.66 (multiplet, 24H); 4.07~4.20 (triplet, 2H); 4.47~4.59 (doublet, 1H); 6.91~8.17 (multiplet, 12H).

EXAMPLE 2

Except for using 86.2 g. (0.37 moles) of nonoxythiophenol, the substantially same process as Example 1 was used to obtain 169 g. (84% of theoretical) of (3S, 2S)-3-fluoro-2-methylbutanoic acid 4'-(4-nonoxybenzyloxy)-biphenyl thioester.

EXAMPLE 3

Except for using 90.7 g. (0.37 moles) of decoxythiophenol, the substantially same process as Example 1 was used to obtain 67.5 g. (85% of theoretical) of (3S, 2S)-3-fluoro-2-methylbutanoic acid 4'-(4-decoxybenzyloxy)-biphenyl thioester.

NMR (CDCl$_3$, ppm): δ=0.69~1.66 (multiplet, 28H); 4.07~4.20 (triplet, 2H); 4.47~4.59 (doublet, 1H); 6.91~8.17 (multiplet, 12H).

It is apparent from the foregoing that various changes and modifications may be made without departing from the spirit of the invention.

Accordingly, the scope of the invention should be limited only by the appended claims, wherein what is claimed is:

1. Smectic liquid crystal compounds of optically-active aliphatic β-halogen substituted carboxylic acid 4'-(4-alkoxybenzyloxy)biphenyl thioester defined by the general formula:

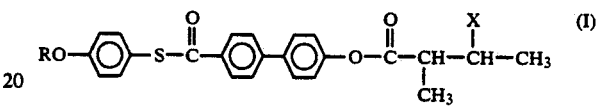

wherein R represents a straight-chained alkyl radical having C$_2$ to C$_{10}$ carbon atoms and X represents a halogen atom, said compounds having high spontaneous polarization.

2. Smectic liquid crystal compounds of optically-active aliphatic β-halogen substituted carboxylic acid 4'-(4-alkoxybenzyloxy)biphenyl thioester defined by the general formula.

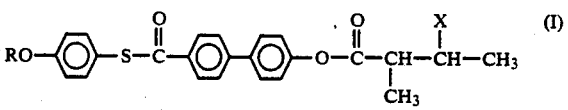

wherein R represents a straight-chained alkyl radical having C$_2$ to C$_{10}$ carbon atoms and X represents a halogen atom, said compounds having high spontaneous polarization, said compound having a thioester as the joining group of the phenyl and biphenyl groups, two chiral carbons followed one after another, α-chiral carbon having a methyl group and β-halogen substituted chiral carbon.

* * * * *